(12) United States Patent
Wooley et al.

(10) Patent No.: US 9,977,257 B2
(45) Date of Patent: May 22, 2018

(54) MULTIFOCAL LENS DESIGN AND METHOD FOR PREVENTING AND/OR SLOWING MYOPIA PROGRESSION

(71) Applicant: Johnson & Johnson Vision Care, Inc., Jacksonville, FL (US)

(72) Inventors: C. Benjamin Wooley, Jacksonville, FL (US); Noel Brennan, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days. days.

(21) Appl. No.: 15/364,737

(22) Filed: Nov. 30, 2016

(65) Prior Publication Data

US 2017/0276961 A1    Sep. 28, 2017

Related U.S. Application Data

(60) Provisional application No. 62/311,487, filed on Mar. 22, 2016.

(51) Int. Cl.
| | |
|---|---|
| *G02C 7/00* | (2006.01) |
| *G02C 7/02* | (2006.01) |
| *G02C 7/04* | (2006.01) |
| *A61F 2/14* | (2006.01) |
| *A61F 2/16* | (2006.01) |

(52) U.S. Cl.
CPC ............. *G02C 7/044* (2013.01); *G02C 7/027* (2013.01); *A61F 2/1451* (2015.04); *A61F 2/1618* (2013.01); *G02C 2202/22* (2013.01); *G02C 2202/24* (2013.01)

(58) Field of Classification Search
CPC ...... G02C 7/044; G02C 7/04; G02C 2202/24; G02C 7/041; G02C 7/047; G02C 7/042; G02C 7/027; G02C 7/048; G02C 7/06; G02C 7/02; G02C 7/028; G02C 2202/08;
(Continued)

(56) References Cited

U.S. PATENT DOCUMENTS

| | | | |
|---|---|---|---|
| 5,225,858 | A | 7/1993 | Portney |
| 6,116,735 | A | 9/2000 | Wada |

(Continued)

FOREIGN PATENT DOCUMENTS

| | | | | |
|---|---|---|---|---|
| EP | 2990857 A1 * | 3/2016 | ............. | A61F 2/145 |
| EP | 2990857 A1 | 3/2016 | | |

(Continued)

OTHER PUBLICATIONS

EP 2990857A1 NPL.*

*Primary Examiner* — Thomas K Pham
*Assistant Examiner* — Sharrief Broome

(57) ABSTRACT

A multifocal ophthalmic lens has an optic zone that includes at least one first zone having a dioptric power that satisfies a distance refraction need of a patient; and at least one second zone having a dioptric power that is greater than the dioptric power of the at least first zone. The at least one first zone and the at least one second zone are configured so that 1) an image quality on the retina of the patient is superior to the image quality both in front of the retina and behind the retina, and 2) an image quality in front of the retina of the patient is superior to the image quality behind the retina. The multifocal ophthalmic lens prevents and/or slows myopia progression.

4 Claims, 13 Drawing Sheets

(58) Field of Classification Search
CPC .... G02C 7/061; G02C 2202/20; G02C 7/024;
G02C 7/049; G02C 2202/06
USPC ............ 351/159.12, 159.06, 159.74, 159.41,
351/159.73
See application file for complete search history.

(56) References Cited

U.S. PATENT DOCUMENTS

| | | | |
|---|---|---|---|
| 6,196,685 B1 | 3/2001 | Roffman | |
| 2012/0176582 A1* | 7/2012 | Back | G02C 7/041 351/159.12 |
| 2012/0327363 A1 | 12/2012 | Wooley | |

FOREIGN PATENT DOCUMENTS

| | | |
|---|---|---|
| WO | WO2008111856 A1 | 9/2008 |
| WO | WO2010129465 A1 | 11/2010 |

* cited by examiner

MULTIFOCAL LENS DESIGN AND METHOD FOR PREVENTING AND/OR SLOWING MYOPIA PROGRESSION

This application claims priority to U.S. Ser. No. 62/311,487, filed on Mar. 22, 2016 in the U.S. Patent and Trademark Office, the entirety of which is incorporated herein by reference.

BACKGROUND OF INVENTION

1. Field of the Invention

The present invention relates to ophthalmic lenses, and more particularly, to contact lenses designed to slow, retard, or prevent myopia progression. The ophthalmic lenses of the present invention comprise multifocal power profiles that provide foveal vision correction, an increased depth of focus, and an optimized retinal image at a range of accommodative distances that makes the degradation of retinal image quality less sensitive to blur during near work activities, thereby preventing and/or slowing myopia progression.

2. Discussion of the Related Art

Common conditions which lead to reduced visual acuity include myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus in front of the retinal plane and hyperopic eyes focus behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow long enough.

Myopia has a high prevalence rate in many regions of the world. Of greatest concern with this condition is its possible progression to high myopia, for example greater than five (5) or six (6) diopters, which dramatically affects one's ability to function without optical aids. High myopia is also associated with an increased risk of retinal disease, cataracts, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or intended to address symptoms. More importantly, correcting the myopic defocus error of the eye does not slow or retard myopia progression.

Most eyes do not have simple myopia or hyperopia, but have myopic astigmatism or hyperopic astigmatism. Astigmatic errors of focus cause the image of a point source of light to form as two mutually perpendicular lines at different focal distances. In the following discussion, the terms myopia and hyperopia are used to include simple myopia or myopic astigmatism and hyperopia and hyperopic astigmatism respectively.

Emmetropia describes the state of clear vision where an object at infinity is in relatively sharp focus with the crystalline lens relaxed. In normal or emmetropic adult eyes, light from both distant and close objects and passing though the central or paraxial region of the aperture or pupil is focused by the crystalline lens inside the eye close to the retinal plane where the inverted image is sensed. It is observed, however, that most normal eyes exhibit a positive longitudinal spherical aberration, generally in the region of about +0.50 Diopters (D) for a 5.0 mm aperture, meaning that rays passing through the aperture or pupil at its periphery are focused +0.50 D in front of the retinal plane when the eye is focused to infinity. As used herein the measure D is the dioptric power, defined as the reciprocal of the focal distance of a lens or optical system, in meters.

The spherical aberration of the normal eye is not constant. For example, accommodation (the change in optical power of the eye derived primarily though changes to the crystalline lens) causes the spherical aberration to change from positive to negative.

As noted, myopia typically occurs due to excessive axial growth or elongation of the eye. It is now generally accepted, primarily from animal research, that axial eye growth can be influenced by the quality and focus of the retinal image. Experiments performed on a range of different animal species, utilizing a number of different experimental paradigms, have illustrated that altering retinal image quality can lead to consistent and predictable changes in eye growth.

Furthermore, defocusing the retinal image in both chick and primate animal models, through positive lenses (myopic defocus) or negative lenses (hyperopic defocus), is known to lead to predictable (in terms of both direction and magnitude) changes in eye growth, consistent with the eyes growing to compensate for the imposed defocus. The changes in eye length associated with optical blur have been shown to be modulated by changes in scleral growth. Blur with positive lenses, which leads to myopic blur and a decrease in scleral growth rate, results in development of hyperopic refractive errors. Blur with negative lenses, which leads to hyperopic blur and an increase in scleral growth rate, results in the development of myopic refractive errors. These eye growth changes in response to retinal image defocus have been demonstrated to be largely mediated through local retinal mechanisms, as eye length changes still occur when the optic nerve is damaged, and imposing defocus on local retinal regions has been shown to result in altered eye growth localized to that specific retinal region.

In humans there is both indirect and direct evidence that supports the notion that retinal image quality can influence eye growth. A variety of different ocular conditions, all of which lead to a disruption in form vision, such as ptosis, congenital cataract, corneal opacity, vitreous hemorrhage and other ocular diseases, have been found to be associated with abnormal eye growth in young humans, which suggests that relatively large alterations in retinal image quality do influence eye growth in human subjects. The influence of more subtle retinal image changes on eye growth in humans has also been hypothesized based on optical errors in the human focusing system during near work that may provide a stimulus for eye growth and myopia development in humans.

One of the risk factors for myopia development is near work. Due to accommodative lag or negative spherical aberration associated with accommodation during such near work, the eye may experience hyperopic blur, which stimulates myopia progression as discussed above.

Moreover, the accommodation system is an active adaptive optical system; it constantly reacts to near-objects, as well as optical designs. Even with previously known optical designs placed in front of the eye, when the eye accommodates interactively with the lens+eye system to near-objects, continuous hyperopic defocus may still be present leading to myopia progression. Therefore, one way to slow the rate of myopia progression is to design optics that reduces the impact of hyperopic blur on retinal image quality. With such designs, for each diopter of hyperopic defocus the retinal image quality is less degraded. In another sense, the retina is therefore relatively desensitized to hyperopic defocus. In particular, depth of focus (DOF) and image quality (IQ) sensitivity may be used to quantify the susceptibility of the eye to myopia progression as a result of hyperopic defocus at the retina. An ophthalmic lens design with a larger depth of focus and low image quality sensitivity will make the degradation of retinal image quality less sensitive to hyperopic defocus, hence slowing down the rate of myopia progression.

In object space, the distance between the nearest and farthest objects of a scene that appear acceptably sharp is called depth of field. In image space, it is called depth of focus (DOF). With a conventional single vision optical design, a lens has a single focal point, with image sharpness decreasing drastically on each side of the focal point. With an optical design with extended DOF, although it may have a single nominal focal point the decrease in image sharpness is gradual on each side of the focused distance, so that within the DOF, the reduced sharpness is imperceptible under normal viewing conditions.

Image quality (IQ) sensitivity can be defined as the slope of the retinal IQ-defocus curve at an accommodative demand of 1 to 5 diopters. It indicates how image quality changes with defocus. The larger the value of IQ sensitivity, the more sensitive image quality is to defocus error during accommodation.

SUMMARY OF THE INVENTION

The ophthalmic lenses of the present invention comprise multifocal power profiles that provide foveal vision correction, an increased depth of focus, and an optimized retinal image at a range of accommodative distances that makes the degradation of retinal image quality less sensitive to blur during near work activities, thereby preventing and/or slowing myopia progression that overcomes the limitations of the prior art as briefly set forth above.

In accordance with one aspect, the present invention is directed to a multifocal ophthalmic lens having an optic zone comprising at least one first zone having a dioptric power that satisfies a distance refraction need of a patient and at least one second zone having a dioptric power that is greater than the dioptric power of the at least one first zone. The at least one first zone and the at least one second zone are configured so that 1) an image quality on the retina of the patient is superior to the image quality both in front of the retina and behind the retina, and 2) an image quality in front of the retina of the patient is superior to the image quality behind the retina.

In accordance with another aspect, the present invention is directed to a method of designing a multifocal ophthalmic lens useful for the mitigation of myopia progression. A first dioptric power profile for at least one first zone of a lens is selected, wherein the first dioptric power profile provides distance refraction for a patient. A second dioptric power profile for at least one second zone of the lens is selected, wherein the second dioptric power profile is greater than the first dioptric power profile. A combination of the first and second dioptric power profiles is assessed to determine an image quality on the retina, an image quality in front of the retina, and an image quality behind the retina. The second dioptric power profile is modified until 1) an image quality on the retina is superior to the image quality in front of the retina and behind the retina and 2) an image quality in front of the retina is superior to the image quality behind the retina.

The present invention provides a method of designing a multifocal optical lens that may be utilized to slow or prevent myopia progression when the lens is worn on eye. The present invention also provides an optimized design for a contact lens that is useful for slowing or preventing myopia progression when the lens is worn on eye. More specifically in accordance with the present invention, by designing a lens with certain values and relationships of image quality in front of the retina, at the retina, and behind the retina while also providing adequate distance vision one may utilize an approach and produce a lens design which may be extremely effective at mitigating myopia progression.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE INVENTION

Multifocal contact lenses designed for presbyopes are optimized to provide suitable vision at distance, intermediate, and near viewing distances. Many of the designs are optimized to provide vision that is good at distance and at near. However, the metrics for multifocal lenses for myopia control are different therefore leading to different designs. Since a patient in need of myopia control, for example a child, may have enough accommodation to be able to focus on near and intermediate objects, the design goals for lenses according to the present invention are different than for known multifocal lenses.

Figure 1:
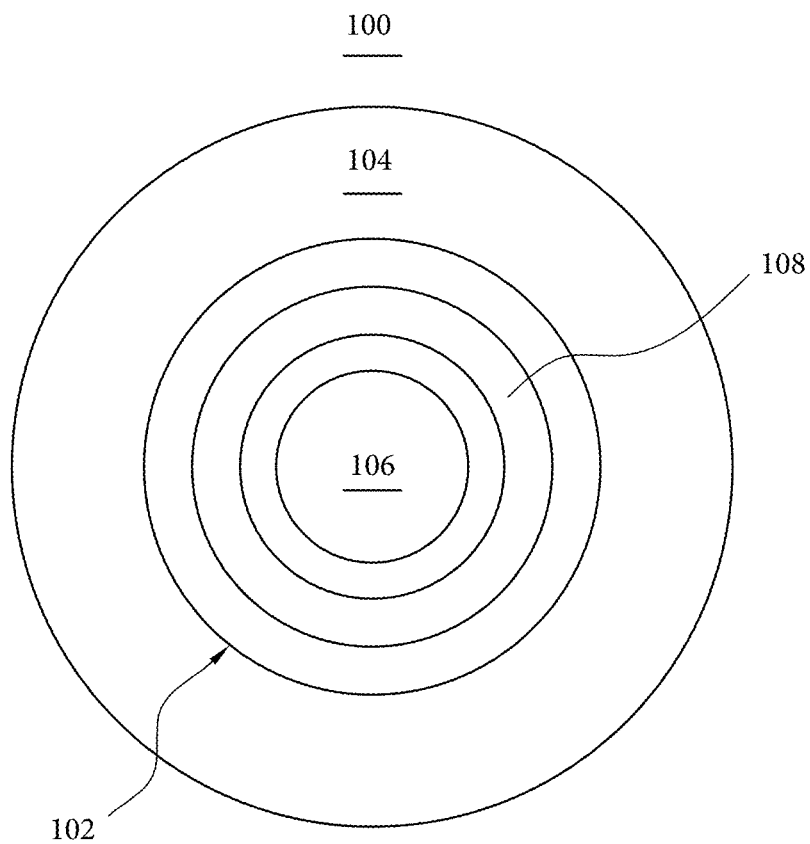
FIG. 1 is a schematic diagram of an exemplary contact lens.

Referring to FIG. 1, there is illustrated a schematic diagram of a contact lens 100. The contact lens 100 comprises an optic zone 102 and an outer region 104. The optic zone 102 comprises an inner or central zone 106 and at least one outer zone 108. In specific embodiments, the diameter of the optic zone 102 may be selected to be 8 mm, the diameter of the substantially circular inner zone 106 may be selected to be 4 mm, and the boundary diameters of an annular outer zone 108 may be 5 mm and 6.5 mm as measured from the geometric center of the lens 100. It is important to note that FIG. 1 only illustrates an exemplary embodiment of the present invention. For example, in this exemplary embodiment, the outer boundary of the at least one outer zone 108 does not necessarily coincide with the outer margin of the optic zone 102, whereas in other exemplary embodiments, they may coincide. The outer region 104 surrounds the optic zone 102 and provides standard contact lens features, including lens positioning and centration. In accordance with one exemplary embodiment, the outer region 104 may include one or more stabilization mechanisms to reduce lens rotation when on eye. The optic zone 102 may consist of multiple zones with each zone having a unique power profile relative to the adjacent zones.

It is important to note that the various zones in FIG. 1 are illustrated as concentric circles, the zones may comprise any suitable round or non-round shapes such as an elliptical shape.

I. Ophthalmic Lens of the Present Invention

According to the present invention, a multifocal ophthalmic lens for a patient comprises an optic zone. The optic zone includes 1) at least one first zone having a dioptric power that satisfies the distance refraction need of a patient, and 2) at least one second zone having a dioptric power that is greater than the power of the at least one first zone. The at least one first zone and the at least one second zone are designed to have an image quality on the retina of the patient that is superior to the image quality both in front of the retina and behind the retina. In addition, the at least one first zone and the at least one second zone are designed so that the image quality in front of the retina is superior to the image quality behind the retina.

The at least one first zone and the at least one second zone may comprise concentric rings having unique dioptric powers in each ring. In specific embodiments, the lens may have from 2 to 10 concentric rings (for example, 2, 4, or 6 rings). In a specific embodiment, the at least one second zone may have a dioptric power that is greater than the at least one first zone. That is, the at least one second zone may have an "ADD" (additional plus power relative to the dioptric power at the center of the lens).

In a specific embodiment, a lens may have at least one first zone (e.g., an inner zone) having a power of −0.5 to −10 D and the at least second zone (e.g. outer zone surrounding the inner zone) may have an ADD that is preferably in the 1.5 to 4 D range. In another specific embodiment, a lens may have at least one second zone (e.g., an outer zone) having a power of −0.5 to −10 D and the at least first zone (e.g. inner zone surrounded by the outer zone) may have an ADD that is preferably in the 1.0 to 4 D range. Thus, the multifocal lens may comprise "distance" rings alternating with ADD rings.

Prior art lenses, like Acuvue® Bifocal (AVB), are designed with spherical surfaces or sections on both the front and back surface. According to the present invention, the multifocal ophthalmic lens may have an aspheric front and back surface. As such, the power within each concentric ring may not be constant, but may show a variation due to spherical aberration. The spherical aberration for lenses with spherical surfaces varies with the lens power (e.g., the refractive prescription of a patient).

The lenses of the present invention may have a prescribed power profile across the lens relative to the refraction that is constant with stock keeping units (SKU) of −3.D, −3.25 D, −3.5 D, and the like. Thus, within the alternating "distance" rings the dioptric power may be substantially the refractive power of the lens, varying to correct for the natural spherical aberration of the eye.

Figure 2:
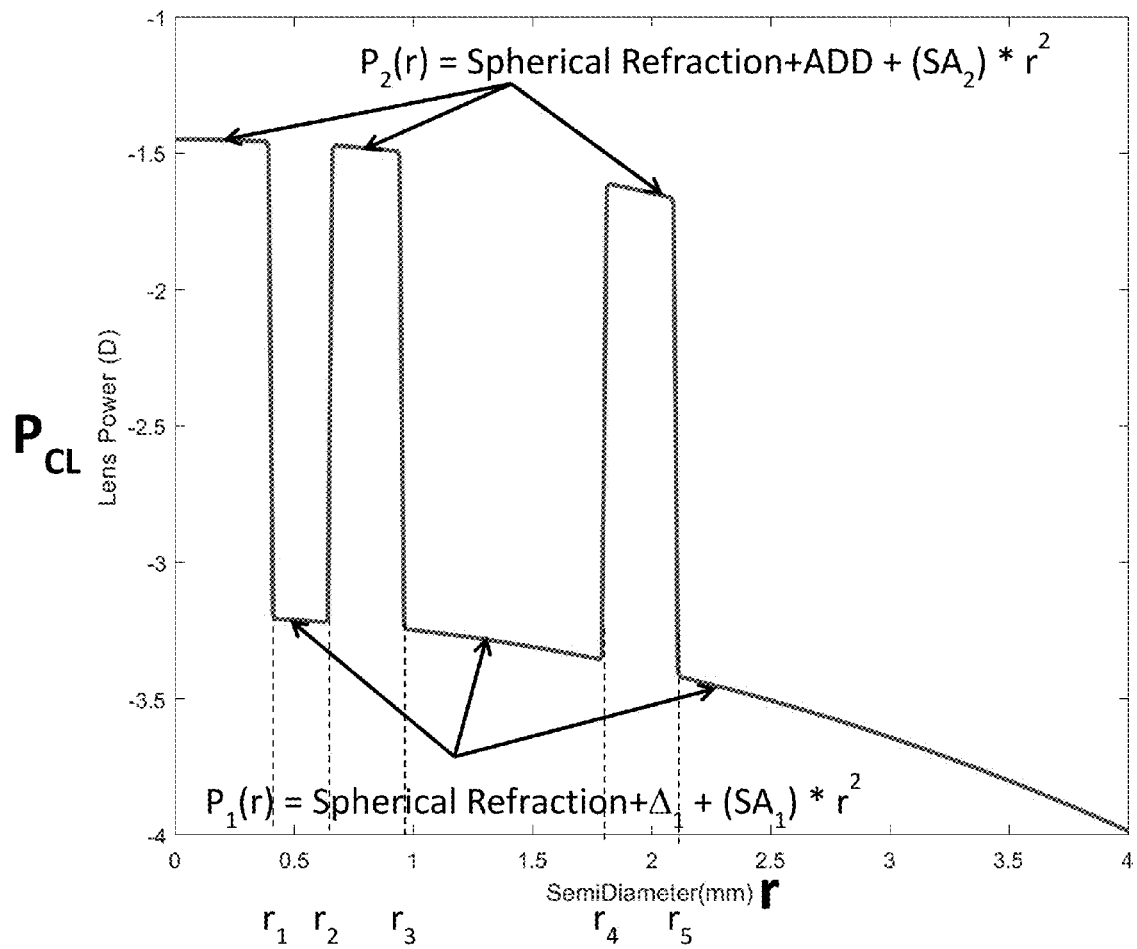
FIG. 2 is a graphical representation of a power profile of a contact lens according to an embodiment of the present invention.

Referring now to FIG. 2, a graphical representation of a power profile of a contact lens according to an embodiment of the present invention is shown. The power, $P_{CL}$, may vary across the semi-diameter (r) of the contact lens. The power corresponds to the axial power in Diopters. The power $P_{CL}(r)$ is the 1/(distance to the focal point in meters) for a ray that enters the lens at a height r from center and optical axis of the lens.

The dioptric power ($P_1$) in the "distance" rings (e.g., rings 1, 3, 5, etc. or alternatively in rings 2, 4, 6, etc.) may be:

$$P_1(r) = \text{Spherical Refraction} + \Delta_1 + (SA_1)*r^2, \quad (1)$$

wherein $SA_1$ is set to be approximately the negative of the spherical aberration of the eye and may be about −0.08 D/mm², r is distance from the center of the lens; Spherical Refraction is the spherical refraction of the patient in Diopters; and $\Delta_1$ is a specified shift in power to ensure that the peak vision is when viewing a distant object with an unaccommodated eye and typically is between −0.25 D and 0.25 D.

The dioptric power ($P_2$) in the ADD rings (e.g. rings 2, 4 6, etc. or alternatively in rings 1, 3, 5, etc.) may be:

$$P_2(r) = \text{Spherical Refraction} + \text{ADD} + (SA_2)*r^2, \quad (2)$$

wherein $SA_2$ typically ranges between 0.0 and −0.15 D/mm² and ADD is typically between 1.0 and 4.0 D, but in specific embodiments may be less than 2.5 D.

The power of the contact lens, $P_{CL}(r)$, is therefore a combination of the $P_1(r)$ and $P_2(r)$ as shown in FIG. 2 with the edges of the zones defined by $r_1, r_2, r_3, r_4, r_5$, respectively. For example, when the "distance" zone is a second zone, as depicted in FIG. 2:

$$P_{CL}(r) = P_2(r) \text{ for } r \le r_1, r_2 < r \le r_3, r_4 < r \le r_5$$

$$P_{CL}(r) = P_1(r) \text{ for } r_1 < r \le r_2, r_3 < r \le r_4, r > r_5 \quad (3)$$

Alternate embodiments may have more or fewer zones or may have $P_1$ and $P_2$ interchanged. In specific embodiments, there may be transition zones between the concentric rings that provide smoothly varying power from one concentric ring to the next.

For myopia control, multifocal design goals according to the present invention include the following:
1. Adequate distance vision (e.g., 20/25 or better or, in specific embodiments greater than −1.0 in −10 log MAR units) with minimal objectionable image artifacts.
2. The image quality on the retina is superior to the image quality in front of the retina and behind the retina.
3. The image quality in front of the retina is superior to the quality of the image behind the retina, when viewing an object at any distance and at pupil sizes from 1 mm to 7 mm (for example, from 3 mm to 6 mm) in diameter.

These goals may be accomplished by ensuring that 1) peaks of through-focus vision curves, as discussed below, are at the 0.0 D defocus position and 2) the through-focus curves are asymmetric about 0.0 D, with the best image quality being on the minus defocus side.

II. Measurement of Image Quality

Any suitable vision metric may be used to measure image quality or visual acuity, for example, Area of Modulation Transfer Function (AMTF); strehl ratio; neural sharpness as in Thibos et al., *Accuracy and precision of objective refraction from wave front aberrations*, Journal of Vision (2004) 4, 329-351; or predictive modeling using pupil sizes and luminance levels to calculate monocular visual acuity (in −10 log MAR units) as described as follows.

Equation 4 gives the wave front, W, of the contact lens plus eye as $$W(R) = \int_0^R r[P_{CL}(r) - \text{Spherical Refraction} + SA_{eye} * r^2] dr \qquad (4)$$

wherein R gives the radial distance from the center of the lens (and eye and wave front), Spherical Refraction is in D, and $SA_{eye}$ is the spherical aberration of the eye and is set at 0.08 D/mm² for this calculation. The wavefront, W, assumes a rotationally symmetric lens; however, to be more accurate, the wavefront may be given in Cartesian coordinates. The conversion between Polar and Cartesian coordinates is known. Given the wavefront, W(x,y), the pupil function (PF) is:

$$PF(x, y) = A(x, y) e^{-i \frac{2\pi}{\lambda} W(x,y)} \qquad (5)$$

wherein A(x,y)=1 for r=(x²+y²)^(1/2) less than or equal to (≤) D/2; and
wherein A(x,y)=0 for r greater than (>) D/2 and the wavelength λ is 0.555 microns. The pupil function PF(x,y) is the complex amplitude within the pupil, and is zero outside of the pupil, i.e., A(r)=0 for r greater than (>) D/2, where D is pupil diameter.

The amplitude point spread function (PSFa) of an optical system, in this case the lens plus eye, is given as the Fourier transform of the 2-dimensional pupil function PF(x,y) and is:

$$PSFa(u,v) = \iint PF(x,y) e^{-i \cdot 2\pi \cdot (u \cdot x + v \cdot y)} dx dy \qquad (6)$$

with the integration done over the pupil radius. The quantities u and v have frequency units of 1/mm and are related to the angles $\Theta_x$ and $\Theta_y$ which are the angles in the x and y directions with units of radians in object space:

$$\theta_x = \lambda \cdot u \qquad (7)$$

$$\theta_y = \lambda \cdot v, \qquad (8)$$

wherein λ is the wavelength in mm.

The intensity point spread function, PSF, is:

$$PSF(u,v) = PSFa(u,v) \cdot PSFa^*(u,v) \qquad (9)$$

wherein * refers to complex conjugate.

The optical transfer function, OTF, given as the Fourier transform of the PSF is:

$$OTF(v_x, v_y) = \iint PSF(\theta_x, \theta_y) e^{-i 2\pi \cdot (\theta_x \cdot v_x + \theta_y \cdot v_y)} d\theta_x d\theta_y \qquad (10)$$

where $v_x$ and $v_y$ are in cycles per radian.

The modulation transfer function, MTF, is:

$$MTF(v_x, v_y) = |OTF(v_x, v_y)|. \qquad (11)$$

The calculation of MTF from a wavefront as outlined above is known in the art and may be done numerically. In polar coordinates the MTF becomes:

$$MTF(v, \Theta) \qquad (12)$$

where ν is the radial frequency:

$$v = \sqrt{v_x^2 + v_y^2} \qquad (13)$$

and Θ is the angle.

The average MTFa is:

$$MTFa = \frac{1}{2\pi} \int_0^{2\pi} MTF(v, \Theta) d\Theta \qquad (14)$$

The weighted area of the MTF (WA) is calculated according to the equation:

$$WA = \int_0^{20 cycles/deg} MTFa(v)^2 \cdot NCSF(v, D, L)^2 dv \qquad (15)$$

wherein MTFa is calculated as in Equation 14 and is a function of the angular frequency, the pupil diameter, and the power profile of the lens plus eye combination, and NCSF is the neural contrast sensitivity function and depends upon the frequency, pupil diameter (D) and luminance (L) expressed in candelas/m². For a lens design that is not rotationally symmetric, the MTF is calculated as the average of the two-dimensional MTF.

A luminance of 250 cd/m², corresponding to a typical office environment, is exemplary of the invention and the NCSF is:

$$NCSF = \frac{1}{k \cdot \sqrt{2} \sqrt{\frac{2}{T}\left(\frac{1}{X_0^2} + \frac{1}{X_{max}^2} + \frac{v^2}{N_{max}^2}\right)\left(\frac{1}{\eta \cdot p \cdot E} + \frac{\Phi_0}{1 - e^{-(v/v_0)^2}}\right)}} \qquad (16)$$

with $$E = \frac{\pi \cdot D^2}{4} \cdot L \qquad (17)$$

wherein L is the luminance (250 cd/m²),
D is the pupil diameter in mm,
and E is the illuminance in Td.

The Equation 16 constants are as follows:
k=3.0;
T=0.1 seconds;
$X_0$=2 degrees;
$X_{max}$=12 degrees;
$N_{max}$=15 cycles;
η=0.03;
p=1.247×10⁶ photons/second/degree²/Td;
ν is frequency in cycles/degree;
$v_0$=7 cycles/degree; and
$\Phi_0$=3.0×10⁻⁸ sec degree².

Descriptions of NCSF may be found, for example, in Barten, "Contrast Sensitivity of the Human Eye and its Effects on Image Quality", SPIE Optical Engineering Press, 1999, which is incorporated herein by reference.

Using the weighted area, WA, the Monocular Performance (MP) in −10 log MAR units can be calculated using the equation:

$$MP = -11.5 + 4.94 * \log 10(WA) - 1.26 * \log 10(WA)^2 + 0.15 * \log 10(WA)^3 \quad (18)$$

with log 10(WA) denoting a log base 10 logarithm of WA. This quantity, which may be calculated from the measured power profiles or the design power profiles of individual lenses, in specific embodiments, may provide the basis for the constraints that describe the lenses of the present invention.

III. Discussion of Specific Lenses

Figure 3A:
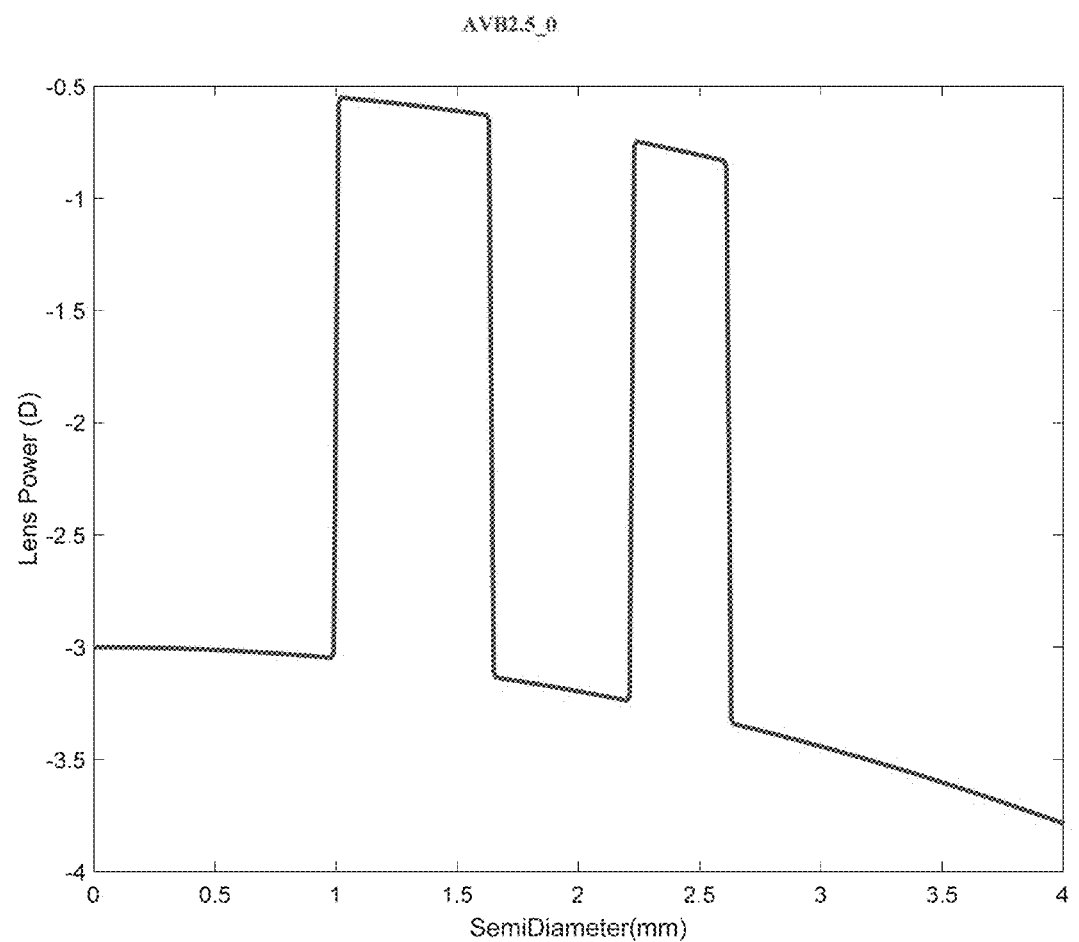
FIG. 3A is a graphical representation of a power profile of a prior art bifocal lens.

FIG. 3A shows a graphical analysis of a power profile for a prior art multifocal lens similar to Acuvue® Bifocal 2.5 D ADD lens. FIG. 3A shows the power profile for a −3.0 D SKU.

Figure 3B:
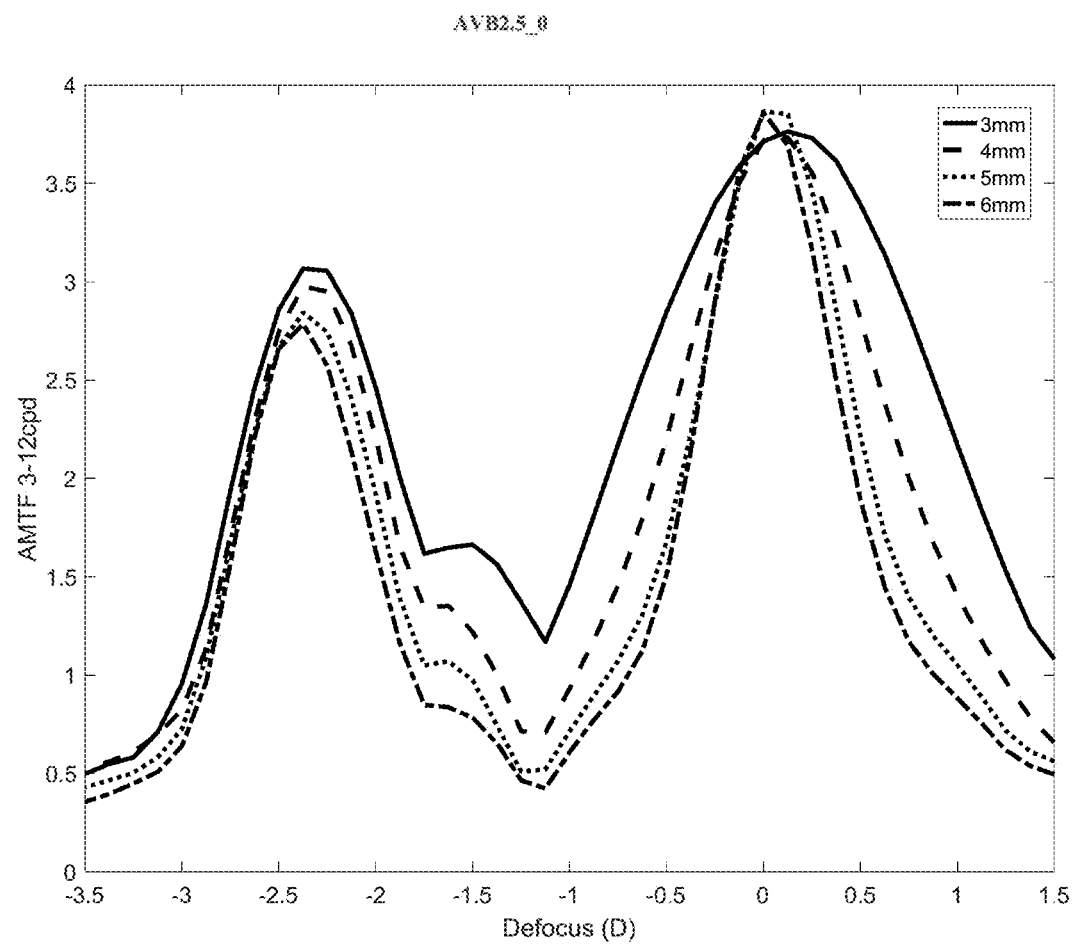
FIG. 3B is a graphical representation of visual acuity versus defocus for the lens.
Figure 3C:
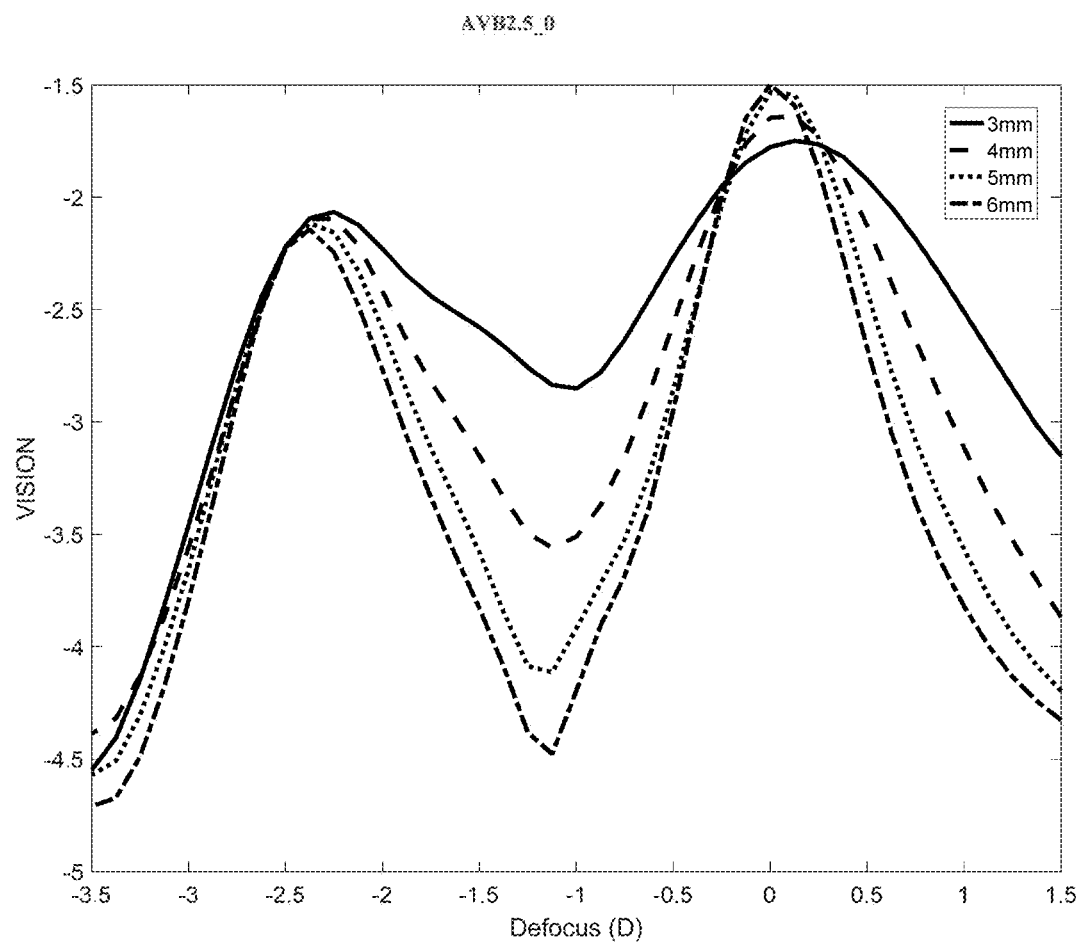
FIG. 3C is another graphical representation of visual acuity versus defocus for the lens.

FIG. 3B shows a calculated visual acuity for Area of Modulation Transfer Function (AMTF) from 3-12 cycles per degree for the lens of FIG. 3A as a function of defocus for 3.0, 4.0, 5.0, and 6.0 D diameter pupil sizes. The 0.0 D defocus corresponds to distance. Minus defocus can be interpreted as showing image quality in front of the retina when viewing a distant object; whereas, plus defocus may be interpreted as showing image quality behind the retina. FIG. 3C shows the predicted visual acuity in units of −10 log MAR calculated using the method described above, which is predictive of clinical results.

Referring to either FIG. 3B or 3C, the above design goals 2-3 are met (e.g., the peaks of the curves at 0.0 D are the maximum values over the whole range; and the through focus vision curves are asymmetric with vision at minus defocus positions in front of the retina, indicating better vision than at positive defocus positions). The first goal, analyzed in reference to FIG. 3C, is not met because for visual acuity at a defocus value of 0.0 D the −10 log MAR unit is less than −1.0. Also, for the 3.0 mm diameter pupil, the secondary peak at about −2 D defocus is nearly the height of the peak at 0.0 D. Thus, for a small pupil size, the patient may not fully accommodate for a near image instead using the near image provided by the design. This will result in the image behind the retina being better quality than the image in front of the retina and providing a growth signal to the eye which can increase myopia.

Figure 4A:
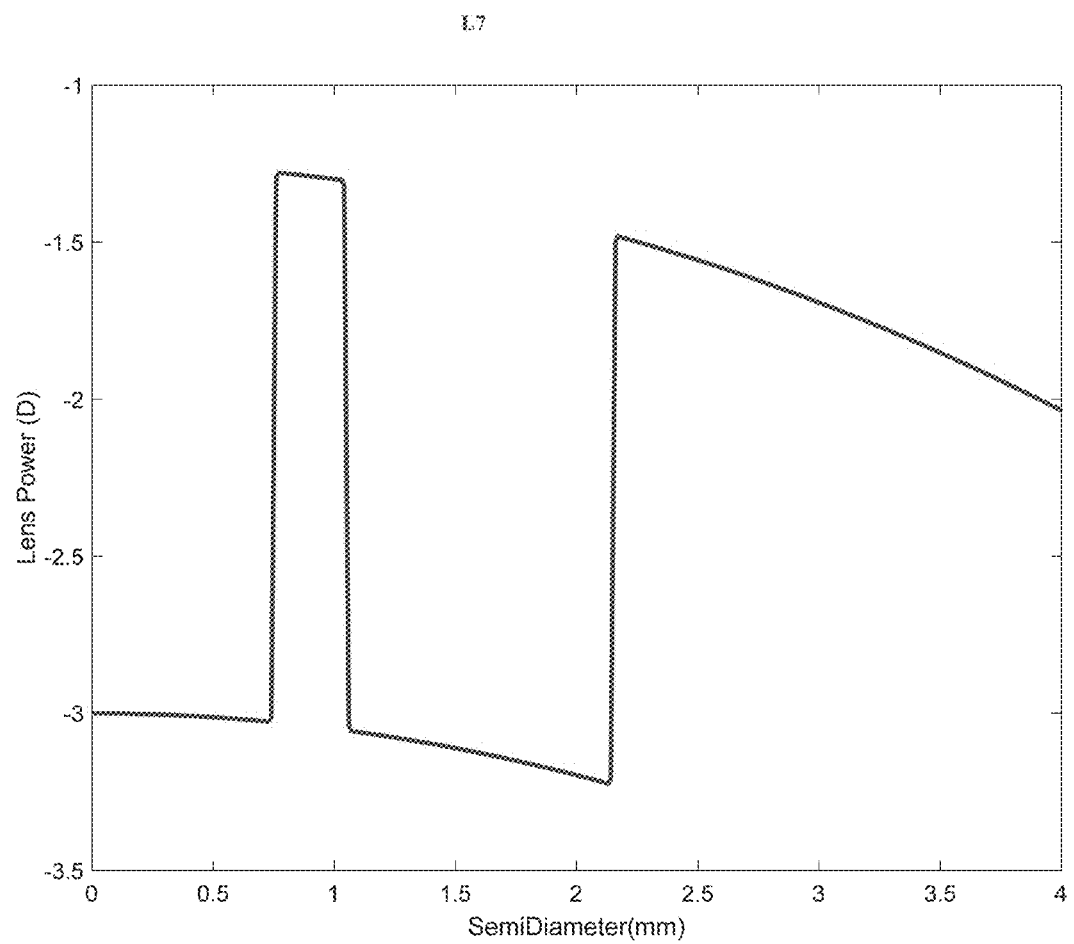
FIG. 4A is a graphical representation of a power profile of a four zone multi-focal lens with a 1.75 ADD (+1.75 D).

FIG. 4A is a graphical representation of a power profile of a four zone multifocal lens according to the present invention. The at least one first zone (e.g., inner zone) has a dioptric power of −3.0 D and alternating "distance" rings have a power substantially similar to −3.0 D, but are corrected for spherical aberration. The at least one second zone (e.g. outer zones) have an ADD of about +1.75 D.

Figure 4B:
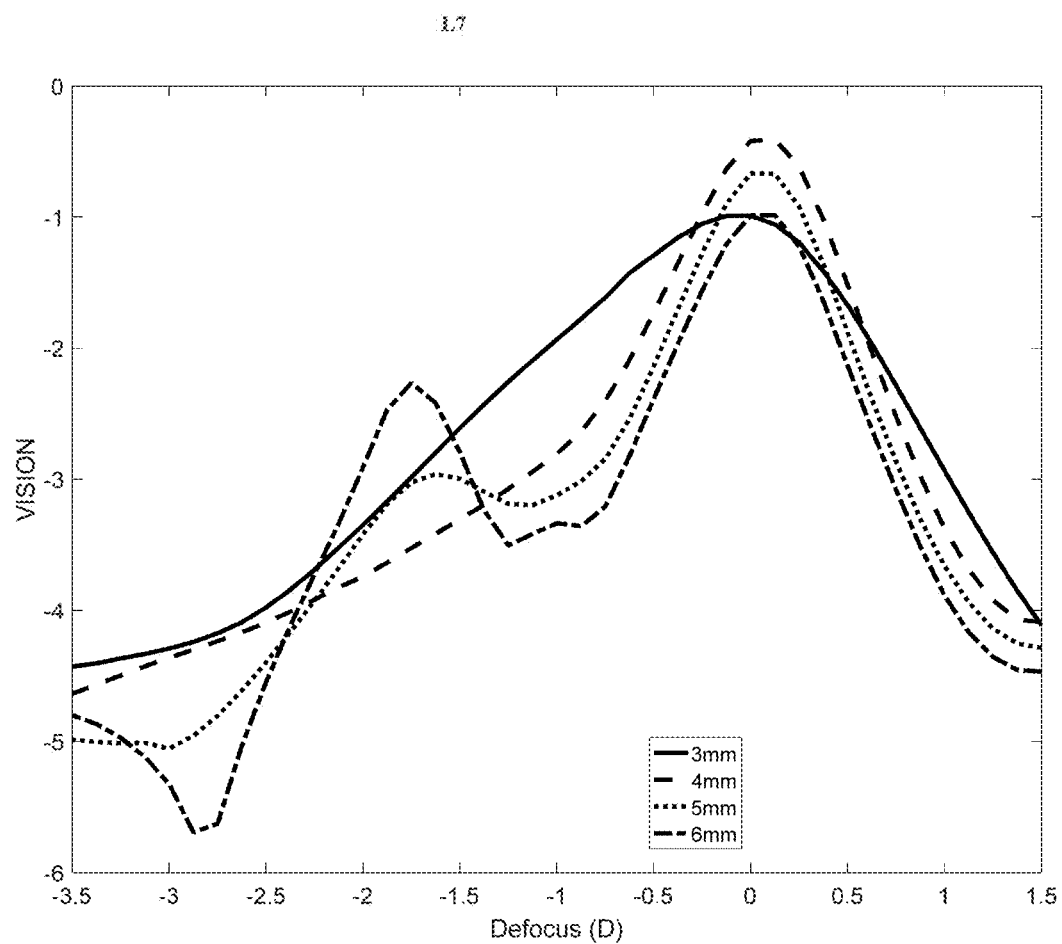
FIG. 4B is a graphical representation of visual acuity versus defocus for the lens.

FIG. 4B is a graphical representation of visual acuity in −10 log MAR units versus defocus for the lens of FIG. 4A for 3.0, 4.0, 5.0, and 6.0 mm pupil diameter sizes. The 0.0 D defocus corresponds to distance. For all pupil diameters, the above design goals 1-3 are met (e.g., the peaks of the curves at 0.0 D are the maximum values over the whole range, the visual acuity at 0.0 D is greater than −1.0 in −10 log MAR units, and the through focus curve is asymmetric with negative defocus values greater than positive defocus values).

Figure 5A:
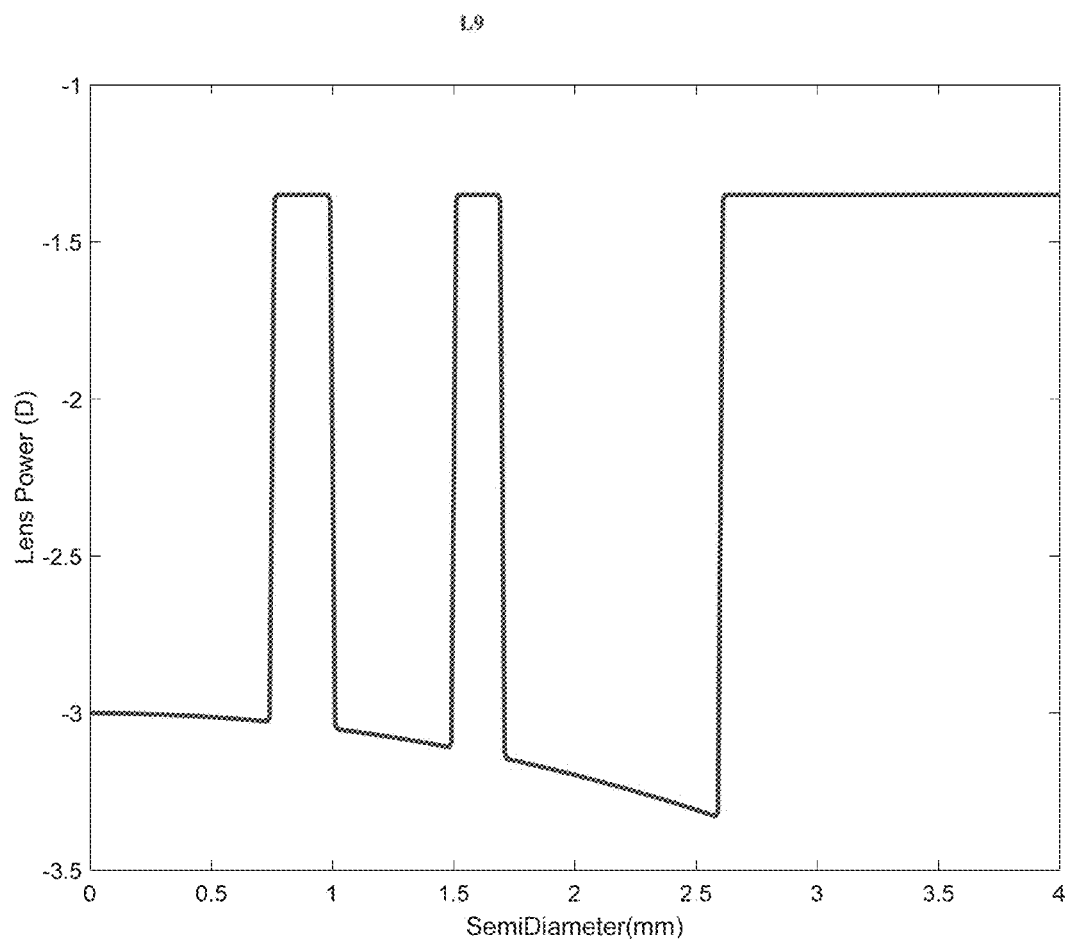
FIG. 5A is a graphical representation of a power profile of a six zone multi-focal lens with a 1.65 D ADD (+1.65 D).

FIG. 5A is a graphical representation of a power profile of a six zone multifocal lens according to the present invention. The at least one first zone (e.g. inner zone) has a dioptric power of −3.0 D and alternating "distance" rings have a power substantially similar to −3.0 D, but are corrected for spherical aberration. The at least one second zone (e.g., outer zones) have an ADD of about +1.65 D.

Figure 5B:
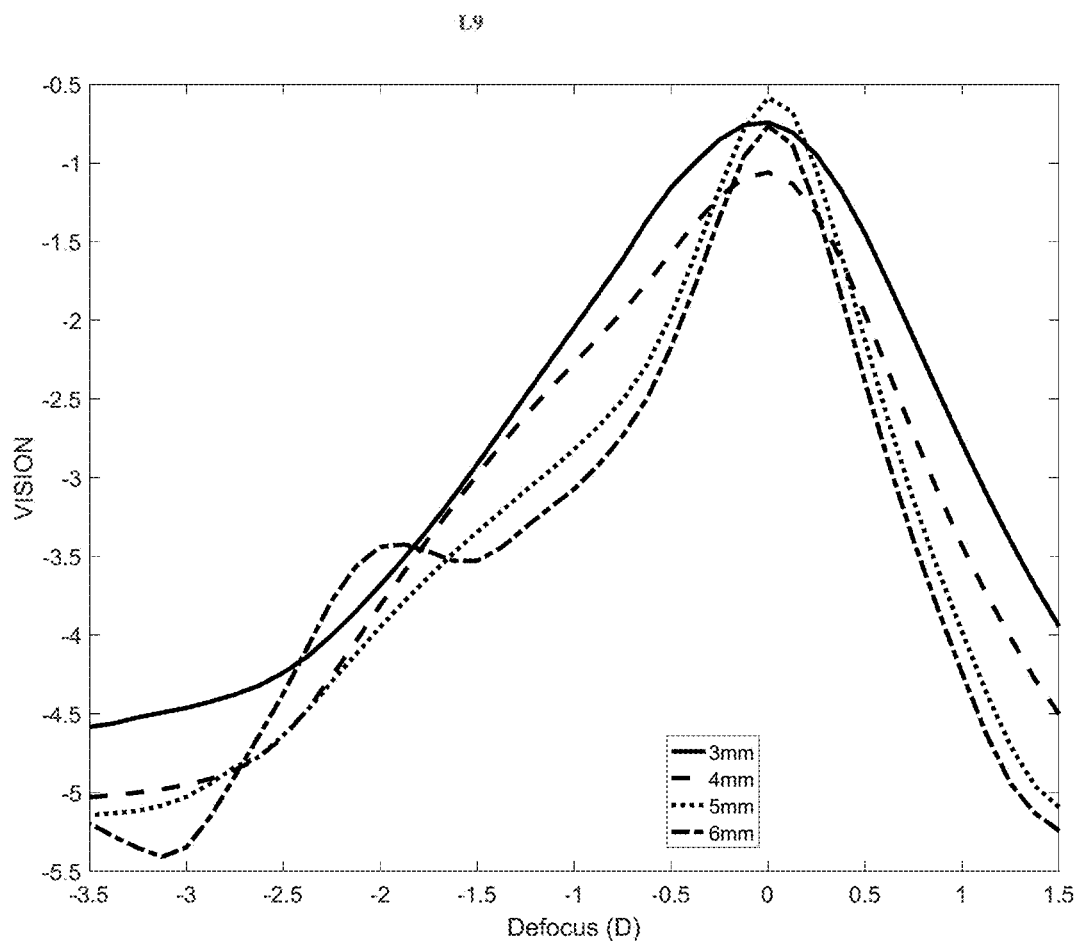
FIG. 5B is a graphical representation of visual acuity versus defocus for the lens.

FIG. 5B is a graphical representation of visual acuity versus defocus for the lens of FIG. 3A for 3.0, 4.0, 5.0, and 6.0 mm pupil diameter sizes. For all pupil diameters, the above design goals 1-3 are met (e.g., the peaks of the curves at 0.0 D are the maximum values over the whole range, the visual acuity at 0.0 D is greater than −1.0 in −10 log MAR units, and the through focus curve is asymmetric with negative defocus values greater than positive defocus values).

Figure 6A:
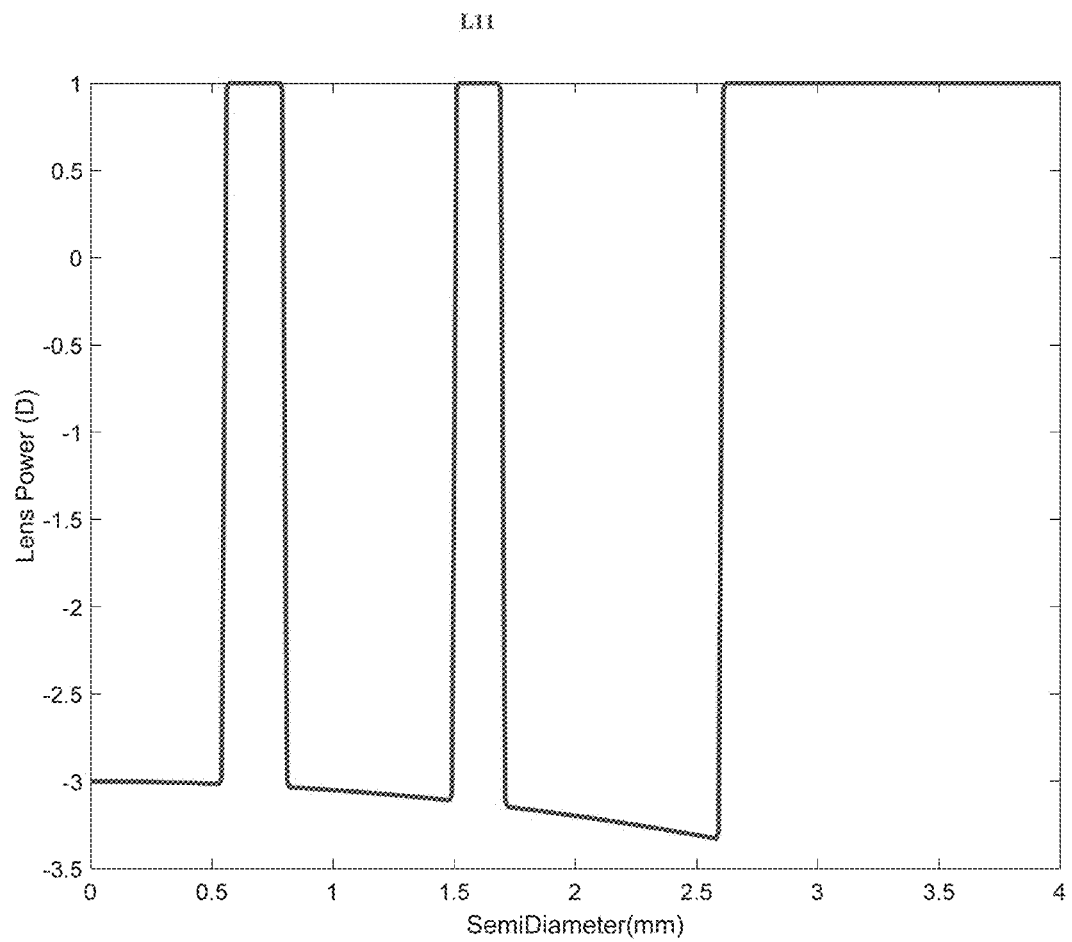
FIG. 6A is a graphical representation of a power profile of a six zone multi-focal lens with a 4 D ADD (+4 D).

FIG. 6A is a graphical representation of a power profile of a six zone multifocal lens according to the present invention. The at least one first zone (e.g., inner zone) has a dioptric power of −3.0 D and alternating "distance" rings have a power substantially similar to −3.0 D, but are corrected for spherical aberration. The at least one second zone (e.g., outer zones) have an ADD of about +4 D.

Figure 6B:
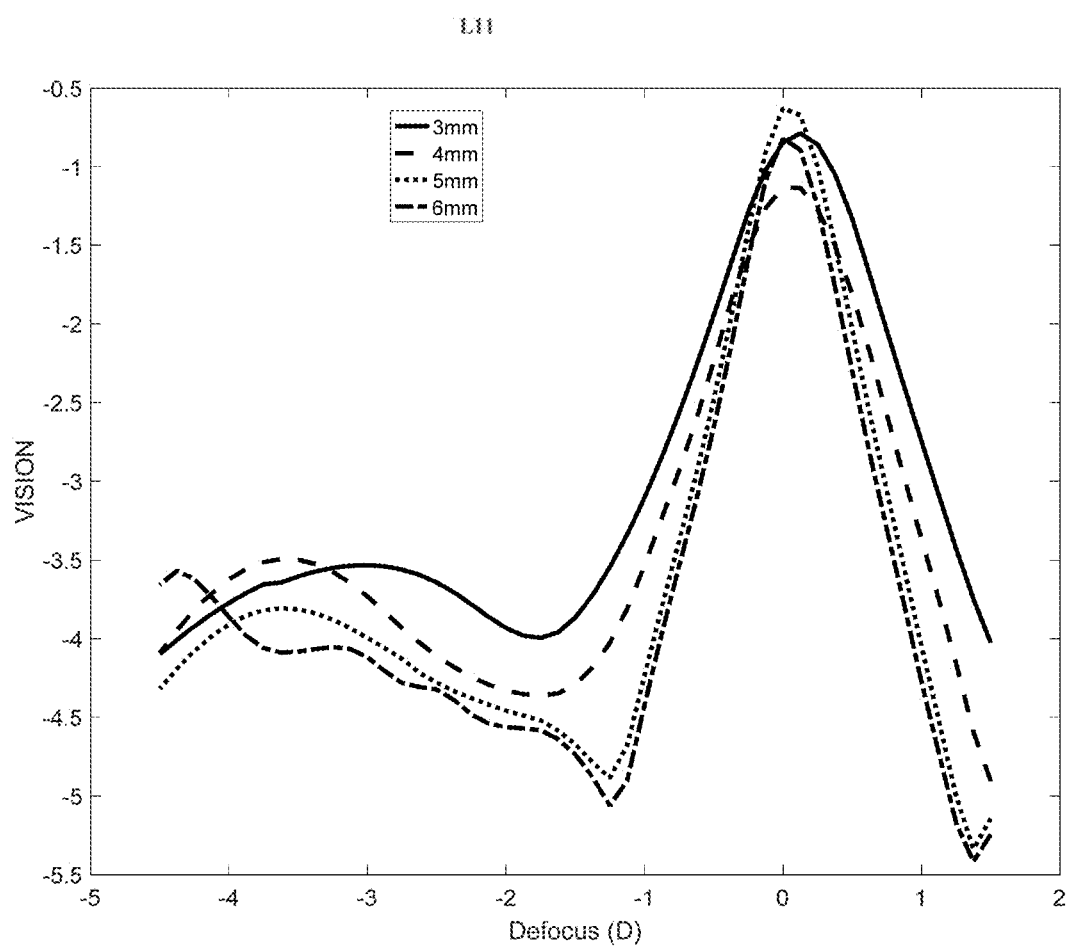
FIG. 6B is a graphical representation of visual acuity versus defocus for the lens.

FIG. 6B is a graphical representation of visual acuity versus defocus for the lens of FIG. 6A for 3.0, 4.0, 5.0, and 6.0 mm pupil diameter sizes. For all pupil diameters, the above design goals 1-3 are met (e.g., the peaks of the curves at 0.0 D are the maximum values over the whole range, the visual acuity at 0.0 D is greater than −1.0 in −10 log MAR units, and the through focus curve is asymmetric with negative defocus values greater than positive defocus values).

Figure 7A:
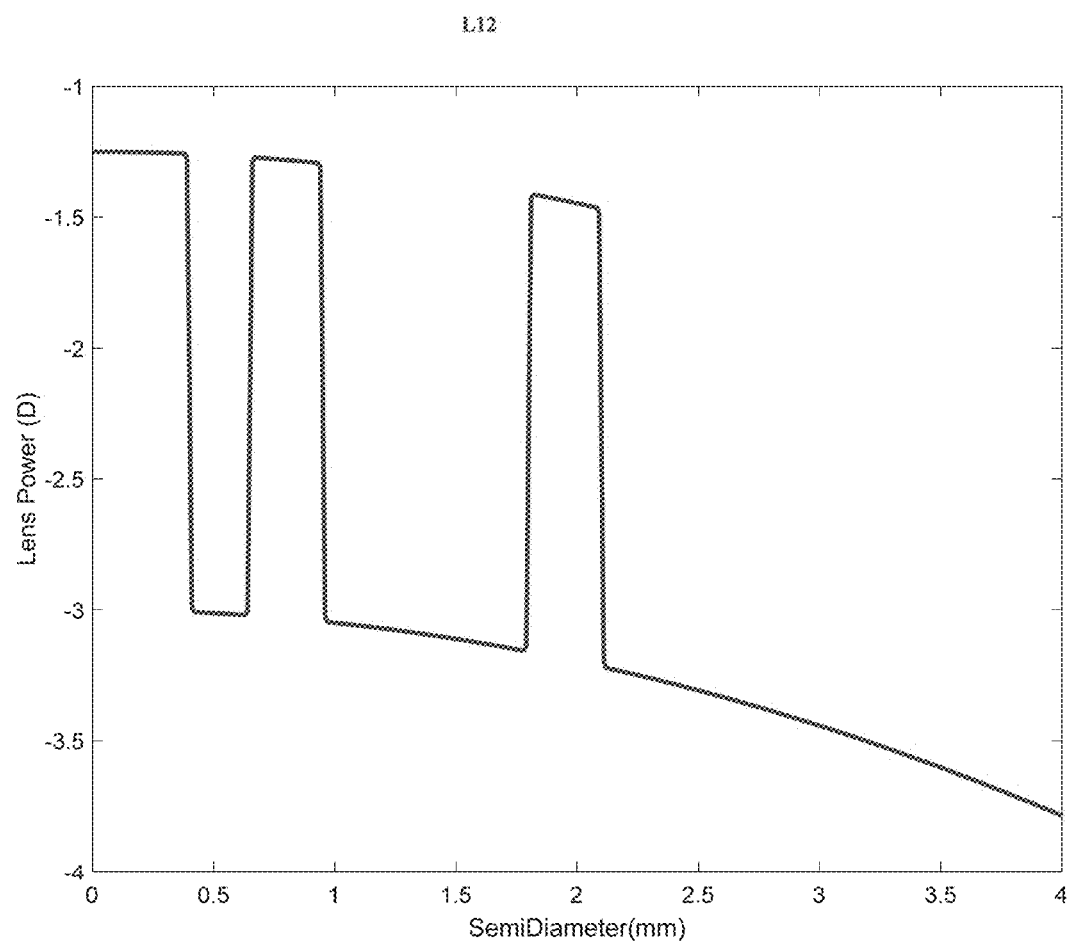
FIG. 7A is a graphical representation of a power profile of a six zone multi-focal lens with a 1.75 D ADD (+1.75 D).

FIG. 7A is a graphical representation of a power profile of another six zone multifocal lens according to the present invention. Unlike the other lenses, a first "distance" zone is not at the lens center, but rather surrounds an ADD zone at the lens center. The first distance zone has a dioptric power of −3.0 D and alternating "distance" rings have a power substantially similar to −3.0 D, but are corrected for spherical aberration. The second zones have an ADD of about +1.75 D.

Figure 7B:
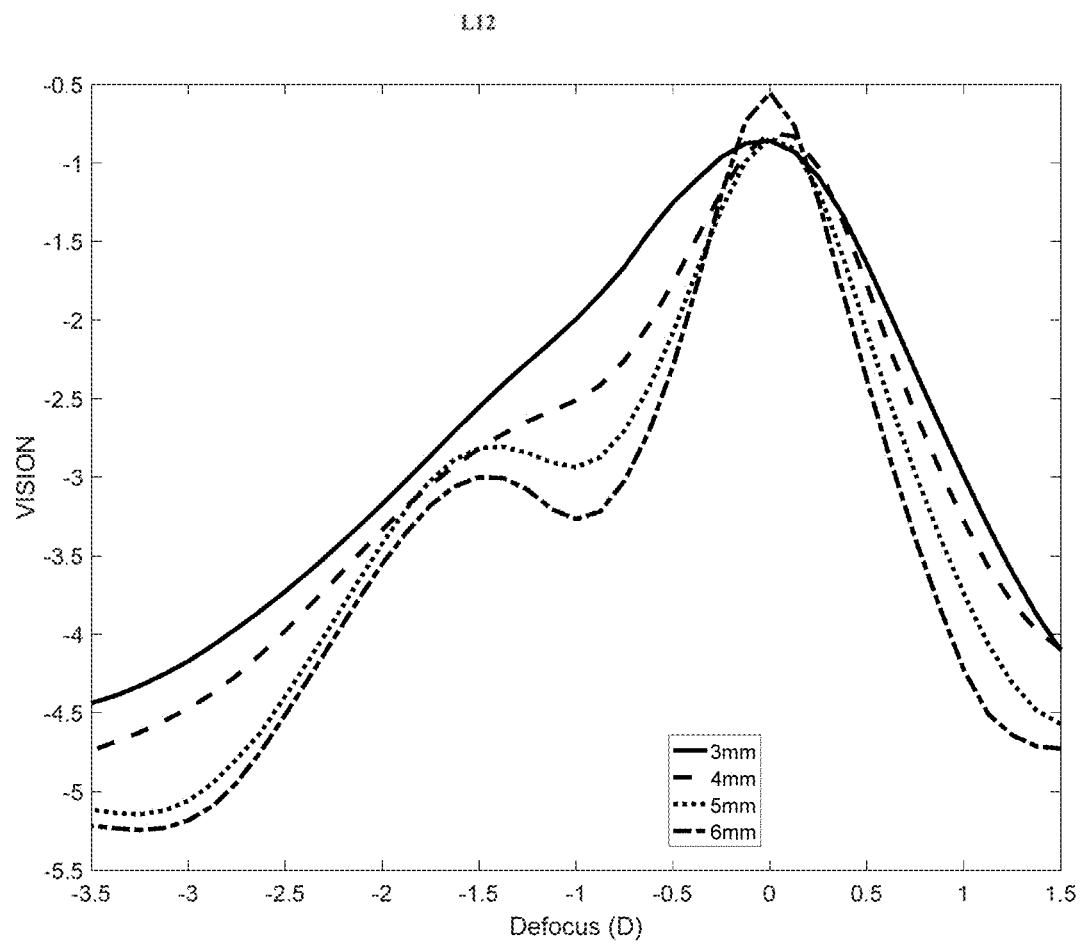
FIG. 7B is a graphical representation of visual acuity versus defocus for the lens.

FIG. 7B is a graphical representation of visual acuity versus defocus for the lens of FIG. 5A for 3.0, 4.0, 5.0, and 6.0 mm pupil diameter sizes. For all pupil diameters, the above design goals 1-3 are met (e.g., the peaks of the curves at 0.0 D are the maximum values over the whole range, the visual acuity at 0.0 D is greater than −1.0 in −10 log MAR units, and the through focus curve is asymmetric with negative defocus values greater than positive defocus values).

Additionally, the designs of the present invention may take into account that spherical aberration changes with accommodation, and lenses can be optimized for pupil sizes of children including pupil size change with accommodation.

It is important to note that as the entrance pupil size of the eye and target vergence/accommodation varies among subpopulations. In certain exemplary embodiments, the lens design may be customized to achieve both good foveal vision correction and myopic treatment efficacy based on the patient's average pupil size and preferred target vergence. Moreover, as pupil size correlates with refraction and age for pediatric patients, in certain exemplary embodiments, the lens may be further optimized towards subgroups of the pediatric subpopulation with specific age and/or refraction based upon their pupil sizes. Essentially, the power profiles may be adjusted or tailored to pupil size to achieve an optimal balance between foveal vision correction, increased depth of focus, and reduced IQ sensitivity.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia, i.e., the loss of the ability of the crystalline lens to accommodate. Contact lenses are available in a variety of forms and are made of a variety of materials to provide different functionality.

Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

It is important to note that the multifocal lens design of the present invention may be incorporated into any number of different contact lenses formed from any number of materials. Specifically, the multifocal lens design of the present invention may be utilized in any of the contact lenses described herein, including, daily wear soft contact lenses, rigid gas permeable contact lenses, bifocal contact lenses, toric contact lenses and hybrid contact lenses. In addition, although the invention is described with respect to contact lenses, it is important to note that the concept of the present invention may be utilized in spectacle lenses, intraocular lenses, corneal inlays and onlays.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A multifocal ophthalmic lens, comprising: an optic zone at least one first zone having a dioptric power that satisfies a distance refraction need of a patients and at least one second zone having a dioptric power that is greater than the dioptric power of the at least one first zone, wherein the at least first zone and the at least one second zone comprises a plurality of alternating distance and ADD rings concentrically arranged, the distance rings having a dioptric power given by $P_1(r)$=Spherical Refraction+$\Delta_1$+$(SA_1)*r^2$, wherein $SA_1$ is approximately $-0.08$ D/mm$^2$, r is distance from the center of the lens, wherein SA is set to be approximately the spherical aberration of the eye, Spherical Refraction is the spherical refraction of the patient in Diopters, and $\Delta_1$ is a specified shift in power to ensure that the peak vision is when viewing a distant object with an unaccommodated eye and ranges between $-0.25$ D and 0.25 D and the ADD rings having a dioptric power given by $P_2r$=Spherical Refraction+ADD+$(SA_2)*r^2$ wherein $SA_2$ ranges between 0.0 and $-0.15$ D/mm$^2$ and ADD ranges between 1.0 and 4.0 D; and an outer zone surrounding the optic zone.

2. The multifocal ophthalmic lens according to claim 1, wherein the optic zone corresponds to a pupil size of about 3 mm to 6 mm.

3. The ophthalmic lens according to claim 1, wherein the ophthalmic lens comprises a contact lens.

4. The ophthalmic lens according to claim 1, wherein the ophthalmic lens comprises an intraocular lens, a corneal inlay, or a corneal onlay.

* * * * *